United States Patent [19]

Yoshikura et al.

[11] Patent Number: 5,766,919

[45] Date of Patent: Jun. 16, 1998

[54] REPLICATION OF HEPATITIS C VIRUS GENOME AND IDENTIFICATION OF VIRUS HAVING HIGH INFECTIVITY

[75] Inventors: Hiroshi Yoshikura, 644, Nakamachi, Kodaira-shi; Yohko Shimizu, 3-17-23, Nishiwaseda, Shinjuku-ku; Aikichi Iwamoto; Minako Hijikata, all of Tokyo, Japan

[73] Assignees: Hiroshi Yoshikura; Yohko Shimizu, both of Tokyo, Japan

[21] Appl. No.: 654,128

[22] Filed: May 28, 1996

Related U.S. Application Data

[62] Division of Ser. No. 963,490, Oct. 20, 1992, Pat. No. 5,552,310.

[30] Foreign Application Priority Data

Jun. 12, 1992 [JP] Japan ..................... 4-153786
Oct. 19, 1992 [JP] Japan ..................... 7-304351

[51] Int. Cl.$^6$ ................... C12N 7/00; C12N 7/01
[52] U.S. Cl. ............... 435/235.1; 435/239; 436/514
[58] Field of Search ................. 435/235.1, 239; 436/514

[56] References Cited

PUBLICATIONS

Shimizu et al., "Further Studies by Immunofluorescence of the Monoclonal Antibodies Associated with Experimental Non-A, Non-B Hepatitis . . . ", Hepatology, vol. 6, No. 6, pp. 1329–1333, 1986.

Shimizu et al., "Evidence for in vitro replication of hepatitis C virus genome in a human T-cell line", Proc. Natl. Acad. Sci. USA, vol. 89, pp. 5477–5481, Jun. 1992.

Minowada et al., "Brief Communication: Rosette Forming Human Lymphoid Cell Lines. I. Establishment & Evidence . . . ", J. Nat'l Cancer Inst., vol. 49, pp. 891–895, Sep. 1992.

Peebles, "An In Vitro Focus–Induction Assay for Xenotropic Murine Leukemia Virus, Feline Leukemia Virus C, and the Feline–Primate Viruses RD–114/CCC/M–7", Virology 67, pp. 288–291, 1975.

Weiner et al., "Detection of hepatitis C viral sequences in non-A, non-B hepatitis", The Lancet, vol. 335, pp. 1–3, Jan. 1990.

Hellings et al., "Preliminary Results of Transmission of Experiments of Non-A, Non-B Hepatitis by Mononuclear Leucocytes . . . ", J. Virological Methods, vol. 10, pp. 321–326, 1985.

Kaneko et al., "Rapid & Sensitive Method for the Detection of Serum Hepatitis B Virus DNA Using the Polymerase Chain Reaction Technique", J. Clin. Microbiology, pp. 1930–1933, Sep. 1989.

Feinstone et al., Non–A, Non–B Hepatitis in Chimpanzees & Marmosets, J. Infec. Dis., vol. 144 No. 6, Dec. 1981.

Feinstone et al., "Inactivation of Hepatitis B Virus and Non-A, Non-B Hepatitis by Cloro-form", Inf. & Imm., vol. 41, No. 2, pp. 816–821, Aug. 1983.

Kuo et al., "An Assay for Circulating Antibodies to a Major Etiologic virus of Human Non-A, Non-B Hepatitis", Science, vol. 244, pp. 362–364, Apr. 1989.

Choo et al., "Isolation of a cDNA Clone Derived from a Blood-borne Non-A, Non-B Viral Hepatitis Genome", Science, vol. 244, pp. 359–361, Apr. 1989.

Takahashi et al., "Demonstration of a hepatitis C virus–specific antigen predicted from the putative core gene in the circulation of . . . ", J. Gen. Virol., vol. 73, pp. 667–672, 1992.

*Primary Examiner*—Leon B. Blankford, Jr.
*Attorney, Agent, or Firm*—Foley & Lardner

[57] ABSTRACT

A method for replication of hepatitis C virus genome comprising infecting animal cells that have been infected with mouse retrovirus, with hepatitis C virus, and then culturing those cells. The present invention further provides a method for distinguishing a hepatitis C virus with high infectivity and a hepatitis C virus with less infectivity, comprising centrifugating a sample comprising a virus to be tested in a liquid medium to determine the density of the virus, and assigning the virus to a hepatitis C virus with high infectivity it the density thereof is up to about 1.06 g/ml, and assigning the virus to a hepatitis C virus with less infectivity if the density thereof is at least 1.13 g/ml; a method for distinguishing a hepatitis C virus with high infectivity and a hepatitis C virus with less infectivity, comprising bringing a virus to be tested into contact with an anti-human immunoglobulin, and assigning the virus to hepatitis C virus with high infectivity if the virus does not form an immunocomplex and assigning the virus to a hepatitis C virus with less infectivity if it does form an immunocomplex; and a method for distinguishing a hepatitis C virus with high infectivity and a hepatitis C virus with less infectivity, comprising inoculating a virus to be tested to cells infected with murine retrovirus, culturing the cells, and assigning the virus to a hepatitis C virus with high infectivity if the virus replicates in the cells, or assigning the virus to a hepatitis C virus with less infectivity if the virus does not replicate in the cells.

8 Claims, 6 Drawing Sheets

CHIMPANZEE 1304

IMMUNOPRECIPITATION

WEEKS

FIG. 5B

DIFFERENTIAL FLOTATION CENTRIFUGATION p=1.063 g/ml

WEEKS

REPLICATION OF HEPATITIS C VIRUS GENOME AND IDENTIFICATION OF VIRUS HAVING HIGH INFECTIVITY

This application is a division of application Ser. No. 07/963,490, filed Oct. 20, 1992 now U.S. Pat. No. 5,552,310.

BACKGROUND OF THE INVENTION

1. Field of the Invention

The present invention relates to a method for replication of hepatitis C virus (HCV) genome, cells for said replication and the use of said cells. The present invention also relates to methods for distinguishing a virus having high infectivity and virus having less infectivity. The methods are useful, for example, in a clinical test relating to HCV.

2. Related Art

The genome of HCV, the main cause of transfusion-related non-A, non-B hepatitis, has been cloned (Choo, Q. L. et al., Science, 244, 359–362, 1989). Synthesis of cDNA by reverse transcription of viral RNA and amplification by PCR of the nucleotide sequence of the HCV cDNA has been useful for detecting HCV genome (Weiner, A. J. et al., Lancet, 335, 1–3, 1990). Immunodiagnostic assays for antibodies against HCV proteins have also been developed (Kuo G. et al., Science, 244, 362–364, 1989). Studies with chimpanzees have provided evidence that the virus is probably enveloped (Feinstone, S. M. et al., Infect. Immun. 41, 816–821, 1983), and is approximately 30–60 nm in diameter (He, L. F. et al., Infect Dis., 156, 636–640, 1987). Additional research, however, has been hampered because of the limited availability of chimpanzees and the relatively low titer of the virus in clinical samples.

Hillings et al. reported on the transmission of non-A, non-B hepatitis (presumably hepatitis C) to chimpanzees by inoculation with leucocytes, most probably T leucocytes, derived from either acutely or chronically infected patents or chimpanzees (Hellings, J. A. et al., J. Virol. Methods, 1985). In addition, it was also recently found that lactose dehydrogenase (LDH)-elevating virus, another unclassified enveloped RNA virus, replicates more efficiently in mouse cells when they are superinfected with murine leukemia virus (Inada, T. et al., Gen. Virol., 72, 2437–2444, 1991). EPC Unexamined Patent Publication No. 0,414,475A describes the replication of HCV in a cell line.

On the basis of cloning an HCV gene, methods for detecting the HCV using hybridization with a DNA probe have been developed. However, with the probe hybridization methods, it is impossible to distinguish a virus with high infectivity and a virus with less infectivity. Accordingly, to distinguish same it is necessary to inoculate a chimpanzee with a virus to be tested and test the infection thereof in the chimpanzee. However, since chimpanzees are expensive and the number of chimpanzees available is limited, an in-vitro method to distinguish a highly infective virus and a less infective virus is desirable.

Data on physical properties of HCV are being accumulated. Miyamoto et al. (J. Gen. Viral. 73: 713–718, 1992) estimated the density of HCV virions (as measured by RT/PCR) to be 1.08 g/ml by SDG centrifugation. In potassium bromide, a slightly higher density of 1.10 g/ml has been reported (Takahashi. K. et al., J. Gen. Virol. 73: 667–672, 1992). Bradly et al. (J. Med. Virol. 34: 206–206, 1991) found the density of infectious HCV (as measured by inoculation of chimpanzees) to be 1.09–1.11 g/ml in sucrose.

SUMMARY OF THE INVENTION

As a result of earnest research by the inventors of the present invention to solve the above-mentioned problems, it was discovered that HCV genome can be efficiently replicated by infecting a T cell line that has been infected with mouse retrovirus with HCV and then culturing those cells, thus leading to completion of the present invention. The inventors of the present invention also discovered that HCV genome can be replicated with greater efficiency by infecting HPB cells with HCV and then culturing those cells. Moreover, the inventors of the present invention also discovered that HCV genome can be replicated with even greater efficiency by treating the above-mentioned cells by, for example, limiting dilution method.

Thus, the present invention provides a method for replication of hepatitis C virus genome comprising infecting cells that have been infected with mouse retrovirus, with hepatitis C virus, and then culturing the cells.

Furthermore, the present invention also provides a method for replication of hepatitis C virus genome comprising infecting HPB cells with hepatitis C virus, and then culturing the HPB cells.

Moreover, the present invention also provides cells infected by murine retrovirus and hepatitis C virus, and being able to replicate hepatitis C virus genome.

Furthermore, the present invention also provides HPB cells infected with hepatitis C virus, and being able to replicate hepatitis C virus genome.

Also, the present invention also provides a composition comprising the above-mentioned cells or cell lysate for detection of hepatitis C virus antibody.

Moreover, the present inventor found that in centrifugation in a liquid medium, such as concentration gradient centrifugation, differential flotation centrifugation, or the like, a virus with high infectivity exhibits a density of up to about 1.06 g/ml, while a virus with low infectivity exhibits a density of at least 1.13 g/ml.

Accordingly, the present invention provides a method for distinguishing a hepatitis C virus with high infectivity and a hepatitis C virus with less infectivity, comprising centrifugation of a sample comprising a virus to be tested in a liquid medium to determine the density of the virus, and assigning the virus to a hepatitis C virus with high infectivity if the density thereof is up to about 1.06 g/ml, and assigning the virus to a hepatitis C virus with less infectivity if the density thereof is at least 1.13 g/ml.

The present invention also provides a process for preparation of a hepatitis C virus with high infectivity or a hepatitis C virus with less infectivity, comprising centrifuging a sample comprising viruses in a liquid medium to separate a virus with a density of up to about 1.06 g/ml and a virus with a density of at least 1.13 g/ml, recovering the virus with a lower density as a hepatitis C virus with high infectivity, or recovering the virus with a higher density as a hepatitis C virus with less infectivity.

The present inventors further found that a hepatitis C virus with less infectivity has been bonded to an anti-hepatitis C virus antibody and can form an immunocomplex when it is brought into contact with an anti-human immunoglobulin antibody, while a hepatitis C virus with high infectivity has not be bonded to an anti-hepatitis C virus antibody and cannot form an immunocomplex when it is bought into contact with an anti-human immunoglobulin antibody.

Accordingly, the present invention further provides a method for distinguishing a hepatitis C virus with high infectivity and a hepatitis C virus with less infectivity, comprising bringing a virus to be tested into contact with an 
anti-human immunoglobulin, and assigning the virus to a hepatitis C virus with high infectivity if the virus does not form an immunocomplex and assigning the virus to a hepatitis C virus with less infectivity if it does form an immunocomplex.

The present inventor further found that a hepatitis C virus with high infectivity replicates in animal cells infected with murine retrovirus, while a hepatitis C virus with less infectivity does not replicate in said cells.

Therefore, the present invention also provides a method for distinguishing a hepatitis C virus with high infectivity and a hepatitis C virus with less infectivity, comprising inoculating a virus to be tested to cells infected with murine retrovirus, culturing the cells, and assigning the virus to a hepatitis C virus with high infectivity if the virus replicates in the cells, or assigning the virus to a hepatitis C virus with less infectivity if the virus does not replicate in the cells.

DETAILED DESCRIPTION

The animal cells used in the present invention are preferably human T cells, and more preferably, Molt-4 cells or HPB cells. These cells are widely used by persons with ordinary skill in the art, and can be easily acquired. In the present invention, animal cells infected with murine retrovirus are used for efficient replication of HCV genome. The murine retrovirus is preferably amphotropic murine leukemia virus that exists in the animal cells as complex with sarcoma virus. One of the preferable cell lines in the present invention is the Molt-4 cell line containing a sarcoma virus-amphotropic murine leukemia virus complex, which is referred to as Molt-4Ma.

Molt-4Ma cells are obtained by co-culturing of Molt-4 cells with S+L-mink cells infected with amphotropic murine leukemia virus. After infecting the Molt-4 cells with the amphotropic murine leukemia virus contained in the S+L-mink cells, non-adhering Molt-4 cells are separated from adhering (to the surface of the culture vessel) mink cells by pipetting. Repeating this procedure several times allows mink cells to be completely removed from the Molt-4Ma cells.

HCV can be replicated with greater efficiency in the case of using animal cells infected with murine retrovirus than in the case of using animal cells not infected with murine retrovirus. For example, when the HCV genome is amplified using Molt-4 cells, although the minus strand of HCV was detected in the Molt-4 cells on the 7th day after infection with HCV, when Molt-4Ma cells were used, HCV was detected in the cells on the 3rd day after infection with HCV. Furthermore, the amount of HCV increased until the 7th day.

Other preferable animal cells of the present invention are HPB cells. HPB cells infected with murine retrovirus (referred to as HPB Ma) can be established in the same manner as Molt-4Ma cells. According to the present invention, HCV can be replicated with greater efficiency by the use of HPB cells or HPB Ma cells than in the case of using Molt-4Ma cells.

Also according to the present invention, it was also confirmed that treatment of the above-mentioned Molt-4Ma, HPB Ma or HPB cells by limiting dilution method, etc. allows HCV replication efficiency to be increased several times, or more specifically, 5–10 times.

The HCV infected animal cells of the present invention produce HCV antigen protein. Thus, HCV antibody can be detected using the animal cells of the present invention or their cell lysate. For example, this can be used in diagnosis of HCV.

To distinguish HCV with high infectivity and HCV with less infectivity, HCV to be tested is brought into contact with the above-mentioned animal cells according to a conventional procedure. Since HCV is a positive strand virus, replication of HCV can be confirmed by detecting negative strands of the virus. However, since the amount of HCV in the sample is very low, the replication of HCV may be confirmed by detecting a positive strand of the HCV. According to the present invention, the HCV tested is assigned to HCV with high infectivity if the replication of the HCV in the animal cells is confirmed, while the HCV tested is assigned to HCV with less infectivity if the HCV does not replicate in the animal cells.

The replication of the HCV can be detected by RT/PCR. Namely, replicated viral RNA is transcripted to a single stranded DNA using a reverse transcriptase (RT), and PCR is carried out using the single stranded DNA as a template according to a conventional manner. Details of the RT/PCR method are described in Example 3.

According to another embodiment of the present invention, HCV with high infectivity and HCV with less infectivity can be distinguished according to their physical property, i.e., density. Namely, virion having a density of up to about 1.06 g/ml is highly infective, and virion having a density of at least 1.13 g/ml is less infective. This is shown in detail in Example 4. Note, in Example 4, the plasma H used as a representative of samples containing HCV with high infectivity and the plasma F used as a representative of samples containing HCV with less infectivity were chosen according to an infection test performed on a chimpanzee. As seen in Example 4, both showed high titers if they are tested by quantitative RT/PCR, and therefore high infectivity and less infectivity cannot be distinguished.

Methods for measuring a density of virion include the concentration gradient centrifugation method, and the differential flotation centrifugation method. The concentration gradient csutrifugation method includes the sucrose concentration gradient centrifugation method. In this method, a sample is overlayed on a sucrose concentration gradient of 20 to 60% by weight, and centrifugation is carried out, for example, at 150,000 to 160,000×g for 10 to 20 hours so as to attain equilibrium. Portions of the sucrose medium are taken at different sucrose concentrations, and for each fraction the presence or absence of HCV is detected by, for example, RT/PCR.

In the differential flotation centrifugation, a sample is over layered on a liquid medium having a densiting of for example, about 1.06 g/ml, for example, 1.063 g/ml, and centrifugation is carried out, for example, at 130,000 to 150,000×g for 20 to 24 hours. Next, the floating fraction and the precipitate fraction are tested by, for example, RT/PCR for the presence of HCV.

Since the plasmas H and F have been stored under exactly the same conditions, it is unlikely that the difference in density is caused by inappropriate handling of the plasmas. However, since the plasma H was obtained during an early acute phase of HCV infection, whereas the plasma F was taken during the chronic phase one year from infusion, then it appears that the observed difference in density between plasmas was related to the stage of infection. Therefore, a chimpanzee was infected with the plasma H, and progress of the infection was observed. As a result, as seen from FIG. 5C, an anti-HCV antibody developed 10 weeks after the infection. On the other hand, as seen from FIG. 5B, until the 8th week, the virus occurred in the top fraction in a differential flotation centrifugation, while after the 10th week, the virus occurred in the bottom fraction. This result suggests a relationship between density of HCV and the presence of an anti-HCV antibody.

Considering the above, the plasmas H and F were tested for the presence of an anti-HCV antibody by an immunofluorescence assay. As a result, the plasma H was anti-HCV antibody negative and the plasma F was anti-HCV antibody positive, suggesting that high density HCV was bonded to an anti-HCV antibody, and low density HCV was not bonded to an anti-HCV antibody.

Accordingly, for the plasmas H and F, and others, formation of an immunocomplex with anti-human immunoglobulin was tested, and the results revealed that the plasma H did not form an immunocomplex, and the plasma F formed an immunocomplex. Accordingly, according to a third embodiment of the present invention, a sample containing HCV to be tested is mixed with an anti-human immunoglobulin, and the HCV is assigned to HCV with high infectivity if the HCV does not form an immunocomplex, and the HCV is assigned to HCV with less infectivity if the HCV forms an immunocomplex.

In the above-mentioned method, as the anti-human immunoglobulin, and commercial antibody preparations, such as rabbit anti-human immunoglobulin can be used. Formation of an immunocomplex can be detected using a conventional method such as immunoprecipitation. In this case the detection is preferably carried out by directly detecting viral RNA in a supernatant or a precipitate by RT/PCR. Alternatively, the anti human immunoglobulin may be labeled with a radioistope, fluorescent agent, enzyme or the like, and the label in a supernatant or in a precipitate is measured.

The present methods have various applications. For example, the method wherein HCVs are distinguished by replication in murine retrovirus-infected animal cells can be used to select an antibody or serum having a neutralizing activity, or to screen anti-viral drugs. For example, to determine whether an anti-HCV antibody or a serum has an activity to neutralize HCV, an antibody or serum to be tested and HCV with high infectivity are added to the animal cells and are then cultured. If the replication of the HCV in the animal cells is inhibited, the tested antibody or serum is considered to have a neutralizing activity. Similarly, in the above-mentioned method, a drug to be tested may be added in place of the antibody or serum, and if the replication of HCV in the cells is inhibited, the tested drug may be considered to have the ability to inhibit infection of HCV. In these experiments, the replication of HCV can be determined by detecting a negative strand of HCV RNA by, for example, RT/PCR.

Although various methods for distinguishing HCV with high infectivity and HCV with less infectivity are described in detail, these methods can be applied to obtain HCV with high infectivity or HCV with less infectivity from a mixture thereof. For example, HCV with high infectivity can be recovered from a top fraction of differential flotation centrifugation described above, or from a fraction of concentration (density) gradient centrifugation corresponding to a density of about 1.13 to 1.17 g/ml.

According to the present invention, HCV with high infectivity and HCV with less infectivity can be distinguished and separated in various biological materials including serum, plasma, and liver tissue.

EXAMPLES

The following provides a detailed description of the present invention through Examples.

In the Examples, cDNA/PCR, in situ hybridization and immunofluorescence for detection of viral RNA were performed as described below.

cDNA/PCR

Nucleic acid was prepared from 100 µl of culture supernatant or a pellet of roughly $1 \times 10^6$ cells. 100 µl of HCV-containing serum or normal serum were processed in the same manner. Liver RNA was isolated using the guanidinium thiocyanate/cesium chloride method (Sambrook, J. et al., Molecular Cloning: A Laboratory Manual, Cold Spring Harbor, N.Y.).

The total nucleic acid extracted from the serum or cells was used for cDNA synthesis and the following double PCR using a nested primer (Kaneko, S. et al., J. Clin. Microbiol., 27, 1930–1933). Following the cDNA synthesis, the reaction mixture was diluted with water and boiled for 5 minutes. After cooling, the mixture was incubated with 0.1 µg of RNAse A for 30 minutes at 37° C. followed by removal of residual RNA.

Next, cDNA was amplified in an automated thermocycler. The specificity of the amplified DNA was confirmed by Southern blot hybridization with an internally $^{32}$P-labelled synthetic 40-mer oligonucleotide probe for PCR primer. Design of the primer was performed based on published HCV cDNA sequences (Houghton, M. et al., Eur. Patent Appl. 88310.922 et al., Publication No. 0318216; and, Takamizawa, A. et al., J. Virol., 65, 1105–1113).

Figure 1:
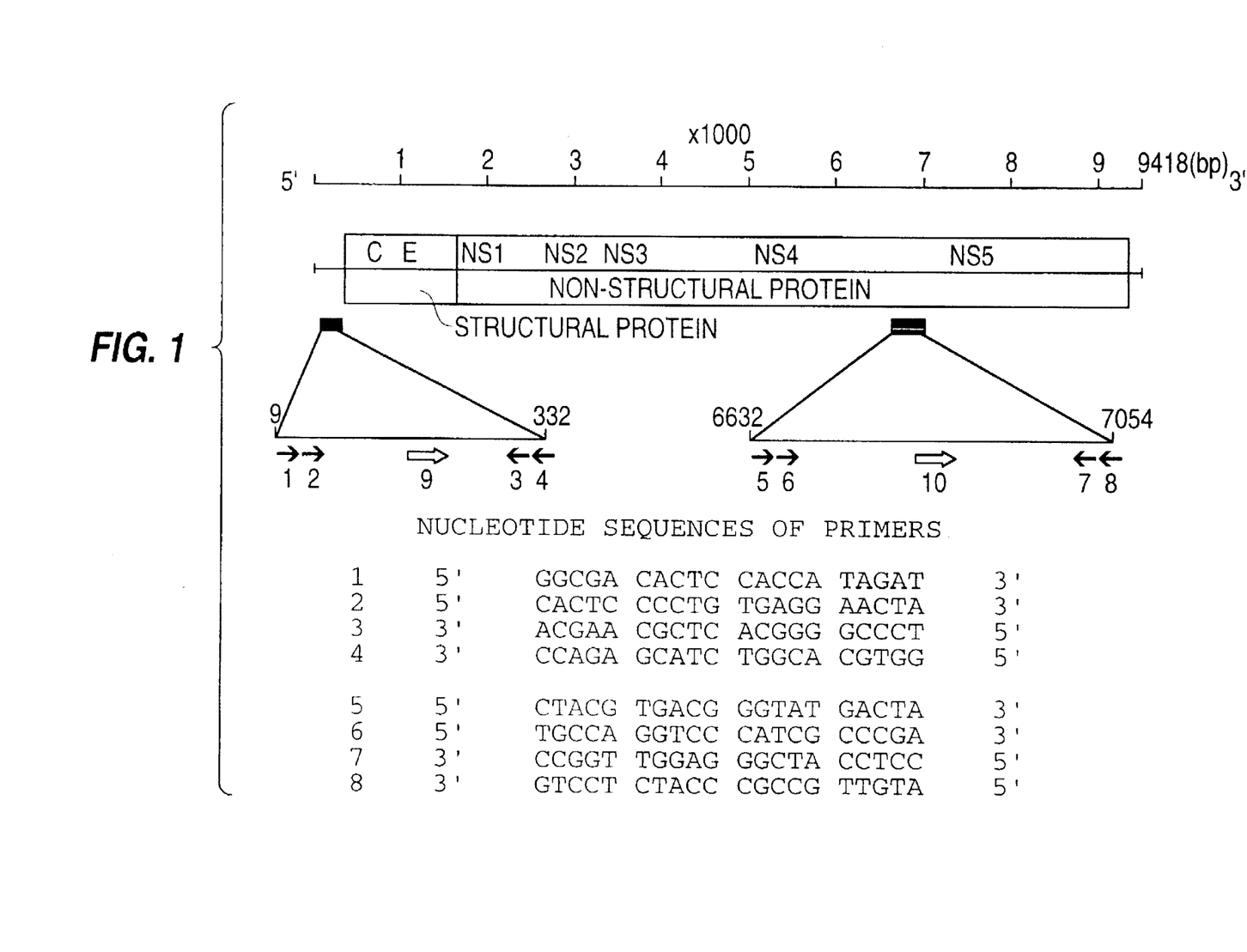
FIG. 1 indicates the nucleotide sequences of the primer used in the present invention, along with their locations in the virus genome.

Two sets of nested primers were used in cDNA/PCR for detection of the HCV sequences. One set was designed to detect the 5' non-codeding region of the genome, while the other set was designed to detect a hypothetical NS5 region. The sequences, orientation and location of the HCV genome of the 20-mer oligonucleotide primer are indicated in FIG. 1. At the stage of reverse transcription, sense primer 1 or 5 was used to prime cDNA synthesis from minus strand HCV RNA. Anti-sense primer 4 or 8 was used to prime CDNA synthesis from plus strand RNA. External primer pairs 1/4 and 5/8 were used followed by the use of internal primer pairs 2/3 and 6/7, respectively, for PCR.

In Situ Hybridization

Detection of intracellular HCV RNA by in situ hybridization was performed using a modification of the method reported by Negro, F. et al. in Hepatology 10, 916–920, 1989. Cells were hybridized overnight at 55° C. in a mixture containing an $^{35}$S-labelled HCV genome strand RNA probe (20,000 cpm/μl) for detection of HCV minus strand RNA. An HCV cDNA fragment (533 bp) coding for a hypothetical core region was severed from C740 plasmid and ligated to Bluescript II (Srategene). A $^{35}$S-labelled genome RNA transcript was then produced using a TranProbe T kit (Pharmacia). This was purified followed by use in the in situ hybridization reaction.

Immunofluorescence

Immunofluorescent staining of virus antigen was performed according to an indirect method previously described (Shimizu, Y. K. et al., Hepatology, 6, 1329–1333, 1986). The monoclonal antibody used in this method was produced by immunizing a mouse with a synthetic peptide based on the published sequences of the HCV genome core and NS4 regions. It was further confirmed that this monoclonal antibody does react with chimpanzee liver infected with HCV, but does not react with normal chimpanzee liver.

EXAMPLE 1

Hepatitis C Virus Source

Serum obtained from chimpanzees, in which F-strain of HCV (Feinstone, S. M. et al., Infect. Dis., 144, 588–595, 1981) had been passaged five times, was used for the source of hepatitis C virus (HCV). Serum was collected 8 weeks after inoculation. This was 5 weeks after initial detection of characteristic hepatitis changes. Plasma H containing $10^{6.5}$ per milliliter of a 50% chimpanzee infective dose ($CID_{50}$) was used for the inoculum.

Molt-4 cell line (Minowada, J. et al., J. Natl. Cancer Inst., 49, 891–895, 1972) and Molt-4 cells infected with a sarcoma virus-amphotropic murine leukemia virus complex (referred to as Molt-4Ma) were used for the T cell line. The Molt-4Ma cell line was established by co-cultivation of S+L-mink cells infected with amphotropic murine leukemia virus (Peebles, R. T., Virology, 67, 288–291, 1975) and Molt-4 cells.

The non-adhering Molt-4 cells were separated from the adhering mink cells by smooth pipetting, and glass-adhering mink cells were removed from the Molt-4 cell culture by several rounds of subculturing by the same method. The cells were preserved in RPMI 1640 supplemented with 8% heat-inactivated fetal bovine serum.

2 ml of the above-mentioned cell suspensions (Molt-4 and Molt-4Ma cells, $3 \times 10^6$ cells/ml) were incubated for 2 hours at 37° C. with 1 ml of the undiluted above-mentioned HCV-containing inoculum. Next, the cells were diluted to $1 \times 10^5$ cells/ml with medium, transferred to culture bottles treated with poly-L-lysine and incubated overnight at 37° C. Next, equal volumes of fresh medium were added to each of the bottles after which incubation was continued.

Although the inoculum contained $10^3$ genomes/100 μl of plus strain viral RNA when measured by PCR, it did not contain minus strands. The presence of intracellular minus strand viral RNA was tested by cDNA/PCR using sense primer 5 for reverse transcription and sense primer pairs 5/8 and 6/7 for PCR after sampling the cell suspensions on days 1, 3, 5 and 7, and separating into supernatant and cell pellets. The locations of these primers within the HCV genome are indicated in FIG. 1.

As a result, minus strand RNA was first detected in infected Molt-4Ma cells on the 3rd day of culturing, and increased to a high level on the 7th day. Similarly, minus strand RNA was first detected on the 7th day after inoculation in infected Molt-4 cells.

As Molt-4Ma cells produced a stronger signal with respect to minus strand viral RNA, these cells were selected for later experiments and preserved for roughly 4 weeks by subculturing at 3–4 day intervals. Those results are indicated in Table 1.

TABLE 1

Detection of HCV RNA in Molt-4Ma Cells

| No. of Days After Inoculation | Detection of Viral Sequences by cDNA/PCR | | |
|---|---|---|---|
| | In Cells | | In Supernatant |
| | Minus Strand | Plus Strand | Plus Strand |
| 0 | | | |
| 1 | − | | − |
| 2 | − | | |
| 3 | − | − | − |
| 4 | − | | − |
| 5 | | | |
| 6 | + | − | |
| 7 | + | − | − |
| 8 | + | + | + |
| 9 | + | + | + |
| 10 | | | |
| 11* | − | + | + |
| 12 | | | |
| 13* | − | − | − |
| 14 | + | + | + |
| 15* | − | + | − |
| 16 | + | + | − |
| 17 | − | − | − |
| 18* | + | − | |
| 19 | − | − | |
| 20 | | − | |
| 21 | − | + | − |
| 22 | | | |
| 23 | − | − | |
| 24* | − | + | |
| 25 | | | |
| 26 | − | − | − |
| 27 | − | | |

*Day on which subculturing was performed.

Although intracellular minus strand viral RNA was unable to be detected for the first 4 days, it was detected from the 6th–9th days after inoculation. Both plus strand HCV sequences and minus strand HCV sequences were sporadically detected in cells during the following 2–3 weeks. Viral sequences were also sporadically observed in the culture supernatant 8–14 days after inoculation.

In order to determine whether or not the occasional disappearance of intracellular HCV sequences from subcultures correlates with the stage of cell reproduction, Molt-4Ma cells were harvested on the 14th day after inoculation, washed once, diluted to $2 \times 10^5$ cells/ml with fresh medium and placed in culture bottles. These were then subcultured for 7 days without changing the medium. The cells were tested with respect to cell reproduction each day, and HCV sequences were tested using a pellet containing roughly $1 \times 10^6$ cells. At this point, plus strand HCV RNA and minus strand HCV RNA demonstrated titers of $10^0$ genomes/cell pellet, by PCR.

In order to confirm these observations, a $^{35}$S-labelled HVC plus strand RNA probe was used in a separate experiment for Molt-4Ma cells harvested on the 7th day after virus inoculation. Minus strand HCV RNA was detected in the infected Molt-4Ma cells. Approximately 1% of the cells were positive. In the case of hybridization with a probe, uninfected Molt-4Ma cells were negative for HCV RNA.

In order to test the expression of virus-coded protein, testing was performed on the putative HCV core antigen and NS4 antigen by indirect immunofluorescence using mouse monoclonal antibody. It was found that Molt-4Ma cells are positive for both antigens on the 7th day after inoculation. Approximately 1% of the cells were positive for both antigens. Uninoculated cells were negative.

Selected experiments were repeated using strains of HCV having carefully determined specificity (Feinstone, S. M. et al., J. Infect. Dis., 144, 588–595, 1981). 0.25 ml of plasma containing H strain HCV ware inoculated into a 2.25 ml sample of cell suspension containing $1.5\times10^6$ Molt-4Ma cells. In this experiment, fresh Molt-4Ma cells were added to the culture at 2–5 day intervals in an attempt to preserve a positive culture for a longer period of time. Intracellular minus strand viral RNA was detected on the 1st day, and again appeared on the 7th day. Positive results were sporadically observed over the course of 3 weeks. The titer of H strain HCV in the inoculum was $10^6$ genomes/100 µl for plus strand HCV RNA, and $10^2$ genomes/100 µl for minus strand RNA.

EXAMPLE 2

2ml of a cell suspension of HPB cells infected with murine retrovirus (HPB Ma) ($3\times10^6$ cells/ml) were mixed with 0.5 ml of undiluted serum obtained from chimpanzees infected with HCV. This mixture was then incubated for 4 hours at 37° C. Although the inoculum contained $10^3$ genomes/100 µl of plus strand HCV RNA when measured by RT/PCR, there were no minus strands detected. Next, the cells were washed twice, suspended in medium at a concentration of $1\times10^5$ cells/ml, and cultured in a $CO_2$ incubator. Pellets containing approximately $1\times10^6$ cells and 100 µl of culture supernatant were sampled at fired intervals, and the presence of HCV RNA was tested by RT/PCR.

Figure 2:
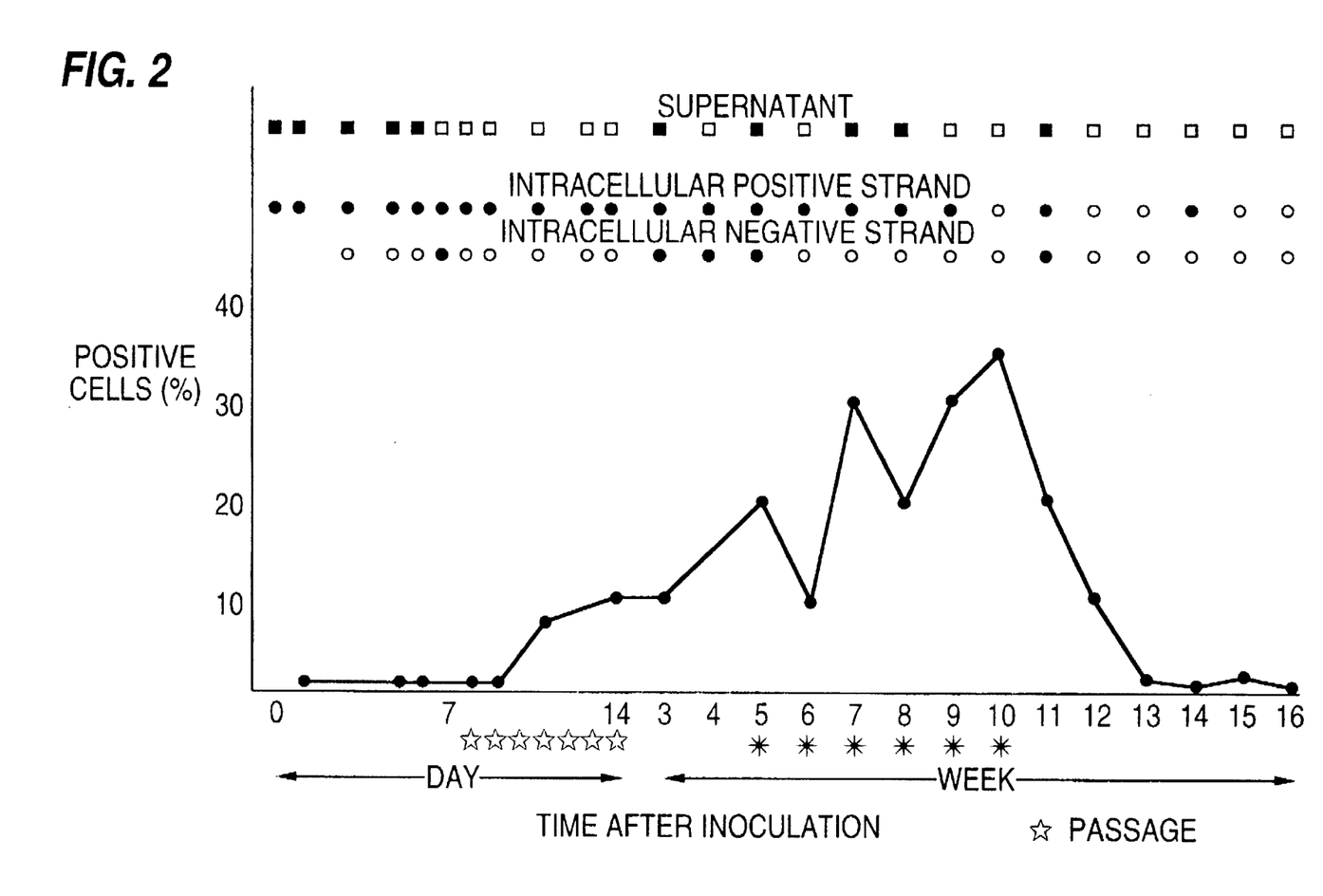
FIG. 2 indicates the course of detection of HCV in the case of using HPB Ma cells.

Moreover, cells were also tested by immunofluorescence using monoclonal antibody to recombinant HCV core protein. Those results are indicated in FIG. 2. Viral sequences were detected continuously in the cells and also detected sporadically in the culture supernatant during the 11th week after inoculation. Intracellular minus strand viral RNA appeared on the 7th day. Approximately 10% of the cells were positive for antigen by immunofluorescence 2 weeks after inoculation, and it was discovered that the number of positive cells increased with time. However, the cells were negative for antigen in the 16th week.

The replication of HCV in HPB cells was further suggested as a result of cycloheximide treatment. It is known that the level of viral prophase mRNA rises following the addition of cells infected with adenovirus. Following treatment with cycloheximide (50 µg/ml, 4 hours), HCV RNA was able to be detected in HPB Ma cells harvested when viral RNA is essentially not detected unless such treatment is performed.

HCV genome can be replicated more efficiently in HPB Ma cells than in Molt-4Ma cells. This is because the positive signal was detected over a longer period of time on the order of 3 months or more.

EXAMPLE 3

Comparison of in vivo infectivity and in vitro genomic titer

As test samples, the following 4 plasmas were used.

Plasma H: collected from patient H during the early acute phase of hepatitis C (7 weeks after blood transfusion).

Plasma F: collected from patient F with chronic hepatitis C approximately one year after transfusion.

Plasma No. 4: obtained from a blood donor. The plasmid had an abnormal alanine aminotransferase (ALT) level and was positive for anti-HCV.

Plasma No. 6: obtained from a blood donor implicated in the transmission of HCV. The plasma had an abnormal alanine aminotransferase (ALT) level and was positive for anti-HCV.

For these plasmas, the results of HCV RNA detection by quantitative RT/PCR and the results of infectivity tests using chimpanzees were compared.

(1) Quantitative RT/PCR

For the detection of HCV RNA, RT and a two step PCR assay with nested primers were performed as described previously (Shimizu, Y. K. et al., Proc. Natl. Acad. Sci. U.S.A. 89: 5477–5481). The sequence of the primer set used for amplification of HCV RNA from plasma H was based on the published sequence of this virus (Ogata et al., Proc. Natl. Acad. Sci. USA 88: 3392–3396, 1991). This primer set detects the putative HCV NS3 region, from map position 4177–4572 of the genome. For amplification of HCV from plasma F, cDNA derived from a chimpanzee passage of HCV from plasma F was partially sequenced and the primers based on the sequence of the putative NS5 region were designed. For plasmas No. 4 and No. 6, a primer set located in the 5' non-coding region was employed, which was shown to be conserved among HCV strains (Bukh, J. et al., Proc. Natl. Acad. Sci. USA 89: 4942–4946, 1992; Okamoto, H., et al., Jpn. J. Exp. Med. 60: 167–177, 1990).

To determined the titer of HCV genomes, RT/PCR was performed on 10-fold serial dilutions of plasmas H, F, No. 4 and No. 6.

(2) In vivo infectivity

For the plasmas H and F, infectivity tests using chimpanzees were carried out according to Feinstone, S. M. et al., J. Infec. Dis. 144: 588–598, 1981, and the infectivity was expressed by a chimpanzee infections dose (CID).

(3) Result

Plasmas H, F, No. 6 and No. 4 yielded titers of $10^7$, $10^5$, $10^5$ and $10^4$ genomes/ml by RT/PCR, respectively and the reported CID of these plasmas was $10^{6.5}$, $<10^2$, $\geq10^5$, and $<10^2$, respectively. Thus, as summarized in Table 2, the ratio of the titers of in vivo infectivity and genomic RNA (as measured by RT/PCR) was approximately 1:1 for plasmas H and No. 6, while it was greater than $1:10^2$–$1:10^3$ for plasmas F and No. 4, indicating that plasmas F and No. 4 contained noninfectious virions at a higher ratio compared to plasmas H and No. 6.

TABLE 2

| Plasma | Genome fiber by RT/PCR[1] | Infectivity fiber in chimpanzee[2] | Ratio of (1)/(2) |
|---|---|---|---|
| H | $10^7$ | $10^{6.5}$ | 1:1 |
| No. 6 | $10^5$ | $\geq10^5$ | 1:1 |
| F | $10^5$ | $<10^2$ | $>10^3$ |
| No. 4 | $10^4$ | $<10^2$ | $>10^2$ |

EXAMPLE 4

Sucrose Density Gradient (SDG)

Figure 3A:
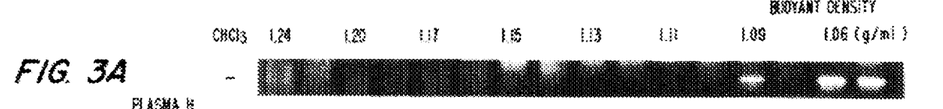
FIG. 3 is a photograph showing the result of sucrose concentration gradient centrifugation of plasma H containing HCV with high infectivity and plasma F containing HCV with less infectivity.

Five hundred µl of a $10^{-2}$ dilution of plasma containing HCV, strain H or F, was layered onto 10.5 ml of a 20–60% w/w sucrose gradient, centrifuged in a Hitachi RPS-40T rotor at 156,000×g for 16 hours at 4° C., and collected in 16 fractions (500 µl each). A 200 µl portion of each fraction was assayed by RT/PCR for the presence of viral RNA. As shown in FIG. 3, the distribution of positive fractions was different in the two plasmas: HCV RNA in plasma H was detected only in fractions with buoyant densities ≦1.09 g/ml (FIG. 3A), while that of plasma F appeared in fractions with higher densities of 1.11–1.17 g/ml as well as in fractions with densities ≦1.06 g/ml (FIG. 3C). Since HCV RNA from the less infectious plasma F was detected mainly at densities higher than those for HCV RNA from the highly infectious plasma H, viral particles distributed in the higher density fractions may have represented noninfectious virions.

To examine this possibility, the plasmas was treated chloroform, which is believed to destroy the infectivity of HCV by disrupting its envelope, and analyzed by SDG equilibrium centrifugation.

Namely, plasmas H and F were treated with chloroform as described by Feinstone et al. (Feinstone, S. M. et al., Infect. Immun. 41: 816–821, 1983). It was demonstrated in their experiments that all infectivity of the diluted plasma H, which contained at least $10^4$ CID/ml, was destroyed by the chloroform treatment.

Five hundred μl of a $10^{-2}$ dilution of plasma H or 500 μl of a $2 \times 10^{-1}$ dilution of plasma F was vigorously mixed with 100 μl of chloroform (20% final concentration) for 10 min and centrifuged. The aqueous phase of each sample was collected and subjected to 20–60% SDG centrifugation as described above.

Figure 3B:
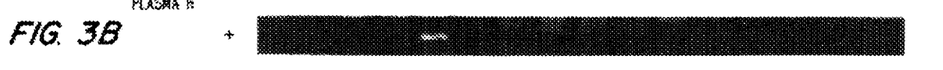
Figure 3C:
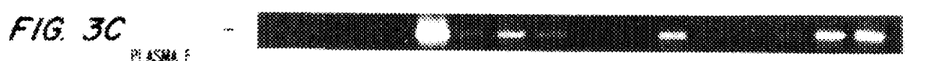
Figure 3D:
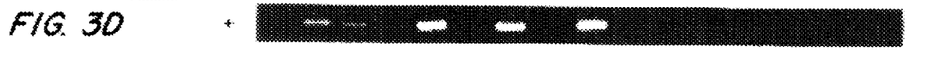
Figure 3E:
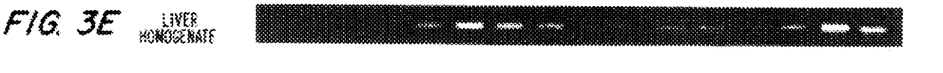

As a result, after chloroform treatment of plasma H, the density of fractions positive for HCV RNA shifted to 1.17 g/ml (FIG. 3B). Following similar treatment of plasma F, HCV RNA in fractions with densities ≦1.11 g/ml disappeared and all HCV RNA was detected in fractions with densities of 1.13–1.17 g/ml (FIG. 3D).

EXAMPLE 5

Differential Floatation Centrifuge

Differential flotation was performed according to the method originally described by Havel et al. for fractionation of plasma low density lipoprotein (LDL) (Havel, R. J. et al., J. Clin. Inves. 34: 1345–1353, 1955). Fifty μl of undiluted plasma H or F was mixed with 8 ml of NaCl solution with a density of 1.006 or 1.063 g/ml and centrifuged in a Hitachi 65T rotor at 139,500×g for 22 hours at 15° C. After centrifugation, 1 ml of the top, 6 ml of the intermediate, and 1 ml of the bottom fractions were collected. A portion of the fractions was assayed by RT/PCR.

Figure 4:
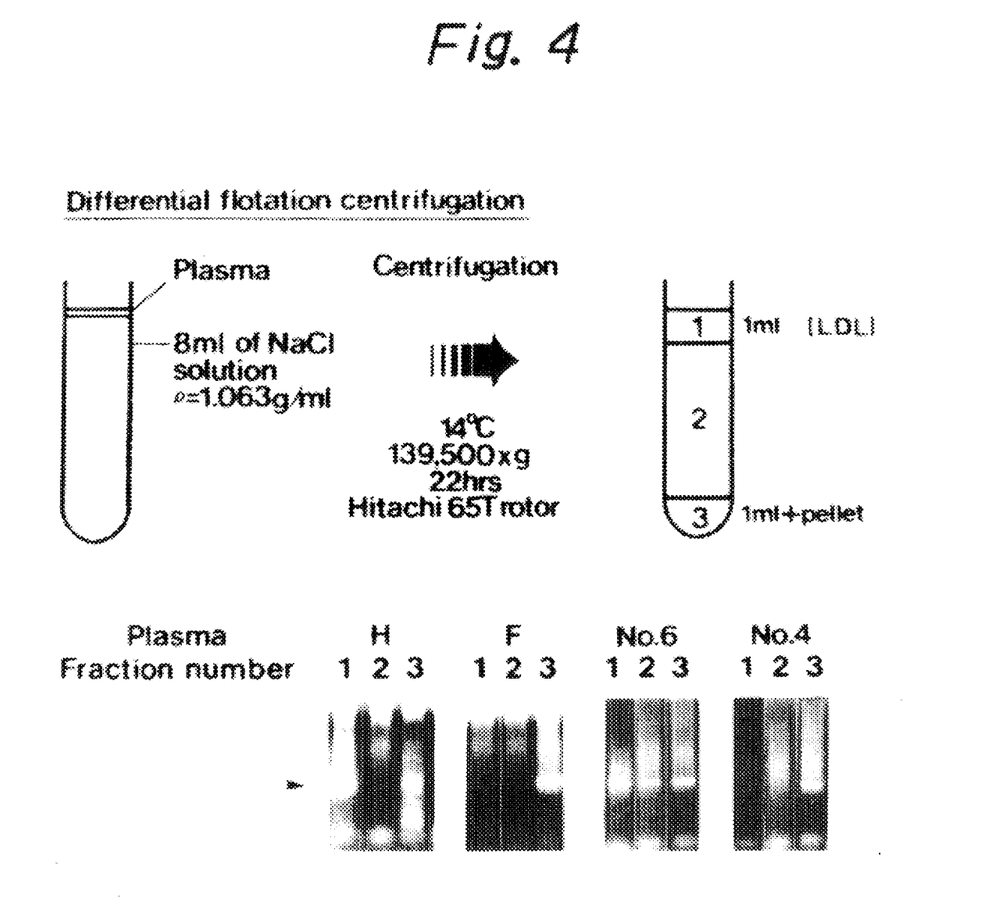
FIG. 4 is a photograph showing the result of differential flotation centrifugation of plasmas H and No. 6 containing HCV with high infectivity, as well as plasmas F and No. 4 containing HCV with less infectivity.

When centrifuged in the solution of 1.006 g/ml, HCV RNA of both plasmas was detected in the bottom fraction (data not shown). In the 1.063 g/ml solution, viral RNA of plasma H was found in the top and bottom fractions, while that of plasma F appeared in the bottom only (FIG. 4). Titration by RT/PCR showed that the ratio of HCV RNA in the top and bottom fractions of plasma H was 10:1. Plasmas No. 4, and No. 6 were similarly centrifuged in NaCl with a density of 1.063 g/ml. HCV RNA of plasma No. 4 was detected in the bottom fraction. HCV RNA of plasma No. 6, on the other hand, appeared in all 3 fractions (FIG. 4), and the ratio of titers in the top and bottom fractions was 1:1. These data suggested that the loss of lipid-containing envelop from virions may be one of the factors responsible for the low infectivity and higher density distribution of HCV from plasmas F and No. 4.

EXAMPLE 6

Infection Experiment in Chimpanzee

Plasmas H and F were prepared and stored identically at −80° C. It was therefore unlikely that the higher density of HCV in plasma F was caused by inappropriate handling after collection. However, plasma H was obtained during the early acute phase of HCV infection, whereas plasma F was taken during the chronic phase (one year after transfusion). It seemed therefore possible that the observed difference in density between the plasmas was related to the stage of infection.

Figure 5A:
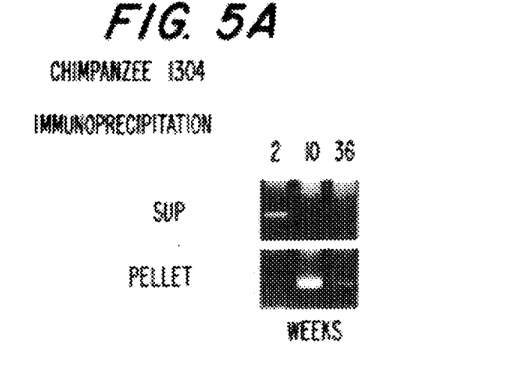
FIG. 5 is a photograph showing the progress of infection of a chimpanzee with HCV with high infectivity.
Figure 5B:
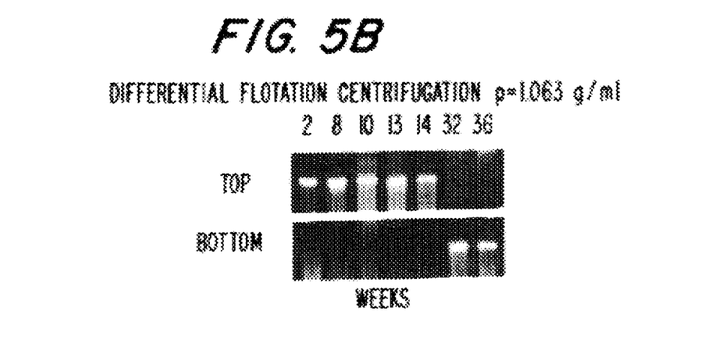
Figure 5C:
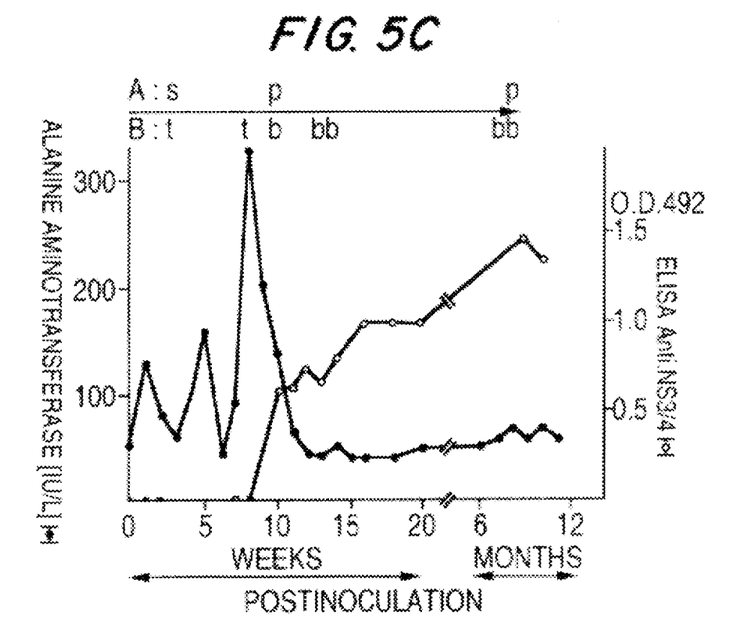

Therefore chimpanzee 1304 was inoculated with 0.5 ml of undiluted plasma containing HCV, strain H, and serum was collected at intervals. Serial serum samples from HCV-infected chimpanzee 1304 were analyzed by flotation centrifugation (1.063 g/ml NaCl solution). As shown in FIG. 5B, most of the viral RNA in sera taken before 8 weeks postinocultion was detected in the top fraction and that in sera taken after 10 weeks was found in the bottom fraction. The time of the shift in density coincided with rising levels of serum transaminase and anti-HCV, specifically, anti-NS3/4 (FIG. 5C).

EXAMPLE 7

Immunofluorescence assay and Immunoprecipitation

As described above, the results from examination of serial sera of chimpanzee 1304 suggested a relationship between the shift of HCV density and the appearance of anti-HCV. To determine if the presence of anti-HCV antibodies was related to the higher density distribution, the plasmas were tested for anti-HCV by IF.

For IF, D8b5 cells expressing HCV core and envelop proteins were employed as target antigens.

The cells were fixed with ethanol, incubated overnight with 2-fold serial dilutions of the plasmas to be tested, washed and incubated with a 1:200 dilution of fluoresceinated goat anti-human IgG (MBL, Japan) for 2 hours at room temperature. As positive controls, monoclonal anti-HCV core and envelop antibodies were used. These antibodies were produced by immunizing mice with recombinant proteins based on the documented sequences of the HCV genome. They were kindly given by Dr. M. Kohara of the Tokyo Metropolitan Institute of Medical Science and detected with fluoresceinated anti-mouse IgG.

Plasmas F and No. 4 gave positive reactions at a titer of 1:160, whereas plasma H was negative and plasma No. 6 was weakly positive at a dilution of 1:10.

To test for the presence of immune complexes of HCV and anti-HCV, imunoprecipitation tests were attempted with anti-human immunoglobulin.

Fifty μl each of a $10^{-2}$ or $10^{-3}$ dilution of plasmas H, F, No. 6 and No. 4 were mixed with an equal volume of a 1:4 dilution of rabbit anti-human immunoglobulin (IgA+IgG+IgM, Cappel, U.S.A.). The mixtures were incubated overnight at 4° C., centrifuged at 680×g for 15 min, and separated into supernatants and pellets. Each pellet was suspended in 100 μl of the diluent. Fifty μl of each supernatant or resuspended pellet was extracted and tested by RT/PCR for the presence of HCV RNA.

Figure 6:
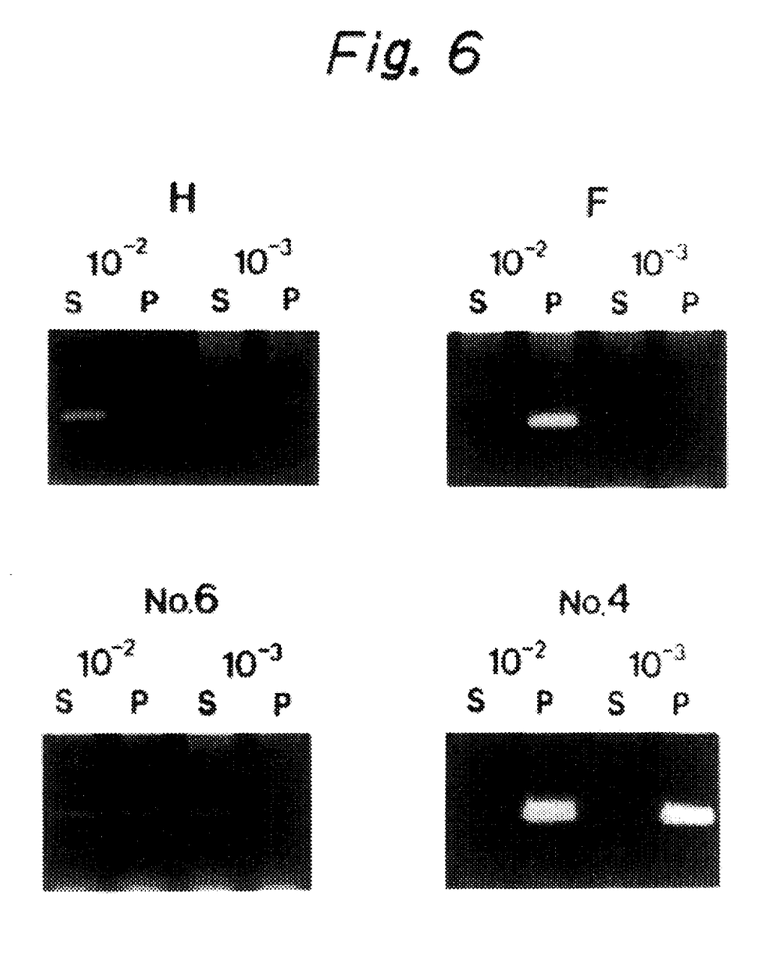
FIG. 6 is a photograph showing the result of immunoprecipitation with anti-human immunoglobulin of plasmas H and No. 6 containing HCV with high infectivity as well as plasmas F and No. 4 containing HCV with less infectivity.

As shown in FIG. 6, all detectable HCV RNA in plasma No. 4 and a large part of HCV RNA in plasma F was found in the pellets, while all HCV RNA in plasma H and a large part of HCV RNA in plasma No. 6 stayed in the supernatants. Thus, in plasmas F and No. 4, most HCV was probably associated with anti-HCV antibodies, while in plasmas H and No. 6 , the virions were free of antibodies.

In addition, sera from chimpanzee 1304 were similarly tested by immunoprecipitation with anti-human immunoglobulin. As shown in FIG. 3A, HCV RNA from sera taken at week 2 was detected in the supernatant, while that from the sera taken at weeks 10 and 35 was found in the pellet.

Example 8

Determination of infective HCV by in vitro Cell Infection

HCV-containing plasma samples used in this Example, as well as genomic titer determined by RT/PCR and chimpanzee infectious dose (CID/ml) thereof are shown in Table 3.

TABLE 3

| Plasma | Source | CID | Genome titer plus-strand | minus-strand |
|---|---|---|---|---|
| H | patient H acute phase | $10^{6.5}$ | $10^7$ | $10^4$ |
| K | patient K chronic phase | NT | $10^5$ | $10^4$ |
| F | patient F chronic phase | $<10^2$ | $10^5$ | $10^5$ |
| N | blood donor | $<10^2$ | $10^4$ | $10^4$ |

HPB-Ma cell line which was used in the present study was obtained by infecting HPB-ALL cells with amphotropic murine leukemia virus pseudo type of murine sarcoma virus. The cloning was done by limiting dilution in 96-multi-well plates to obtain HPB-Ma #10-2.

HPB-Ma cells were suspended at a concentration of $5\times10^5$ cells/ml. One ml of the suspension was mixed with 100 µl of the sample. After incubation for 2 hr, the cells were washed twice with 20 ml culture medium, and suspended in 30 ml. The cell suspension in a volume of 5 ml was distributed into each 25 ml Falcon plastic bottle. One of the bottles was sacrificed daily for detection of HCV genome. To prepare the sample, the well characterized inocula, H and F, were serially 10-fold diluted and used to infect HPB-Ma #10-2.

Since HCV is a positive strand virus, its replication can be evaluated by detection of the negative strand. Accordingly, for the above-mentioned sample, the negative strand was detected by the RT/PCR method. The titer was $10^5$/ml for inoculum H and 10/ml for inoculum F. The infectivity in chimpanzee was $10^{6.5}$/ml for H and 0.1–1/ml for F. The titers in vitro and in vivo well agreed with each other. Table 4 includes the data with other inocula; the correlation between in vivo and in vitro infectivities also holds here.

TABLE 4

| Inoculum | Dilution ($Log_{10}$) | | | | | | in vitro infectivity/ml | in vivo infectivity* |
|---|---|---|---|---|---|---|---|---|
| | −1 | −2 | −3 | −4 | −5 | −6 | | |
| H | NT | + | + | + | ± | − | $10^5$ ($10^4$) | $10^{6.5}$ |
| K | ± | + | − | − | − | − | NT $10^2$ | NT |
| F | ± | − | − | − | − | − | NT 10 (<10) | $<10^2$ |
| N | − | − | − | − | − | − | NT <10 | $<10^2$ |

*: Reported chimpanzee infections doses per ml.
+: Positive at any one occasion during 5 day-observation

We claim:

1. A method of distinguishing a hepatitis C virus with high infectivity and a hepatitis C virus with less infectivity, comprising centrifugating a sample comprising a virus to be tested in a liquid medium to determine the density of the virus, and assigning the density thereof is up to about 1.06 g/ml, and assigning the virus to a hepatitis C virus with less infectivity if the density thereof is at least 1.13 g/ml.

2. A method according to claim 1, wherein the density of the virus is measured by sucrose density gradient centrifugation.

3. A method according to claim 1, wherein the density of the virus is measured by differential flotation centrifugation.

4. A method according to claim 3, wherein the differential flotation centrifugation is carried out using a sodium chloride aqueous solution having a density of about 1.06 g/ml, and assigning the virus to a hepatitis C virus with high infectivity if the virus is transferred to the floating fraction, and assigning the virus to a hepatitis C virus with less infectivity if the virus is transferred to the precipitate.

5. A process for preparation of a hepatitis C virus with high infectivity or a hepatitis C virus with less infectivity, comprising centrifuging a sample comprising viruses in a liquid medium to separate a virus with a density of up to about 1.06 g/ml and a virus with a density of at least 1.13 g/ml, recovering the virus with a lower density as a hepatitis C virus with high infectivity, or recovering the virus with a higher density as a hepatitis C virus with less infectivity.

6. A process according to claim 5, wherein the centrifugation is sucrose density gradient centrifugation.

7. A process according to claim 5, wherein the centrifugation is differential flotation centrifugation.

8. A process according to claim 7, wherein the centrifugation is carried out in a sodium chloride aqueous solution having a density of about 1.06 g/ml, and the hepatitis C virus with high infectivity is recovered from the floating fraction, or the hepatitis C virus with less infectivity is recovered from the precipitated fraction.

* * * * *